United States Patent [19]
Brossi et al.

[11] Patent Number: 5,998,460
[45] Date of Patent: Dec. 7, 1999

[54] PHENYLCARBAMATES OF (−)-ESEROLINE, (−)-N1-NORESEROLINE AND (−)-N1-BENZYLNORESEROLINE: SELECTIVE INHIBITORS OF ACETYL AND BUTYRYLCHOLINESTERASE, PHARMACEUTICAL COMPOSITIONS AND METHOD OF USE THEREOF

[75] Inventors: Arnold Brossi, Bethesda, Md.; Malgarzota Brzostowska, Poznan, Poland; S. Rapoport, Washington, D.C.; Nigel Greig, Silver Spring, Md.

[73] Assignee: The United States of America as represented by the Secretary of the Department of Health and Human Services, Washington, D.C.

[21] Appl. No.: 08/096,207

[22] Filed: Jul. 26, 1993

Related U.S. Application Data

[63] Continuation of application No. 07/861,329, Mar. 31, 1992, abandoned, which is a continuation-in-part of application No. 07/765,746, Sep. 26, 1991, Pat. No. 5,171,750.

[51] Int. Cl.$^6$ .......................... A61K 31/40; C07D 487/04
[52] U.S. Cl. ............................. 514/411; 548/429
[58] Field of Search ............... 548/429; 514/411

[56] References Cited

U.S. PATENT DOCUMENTS

| | | | |
|---|---|---|---|
| 4,900,748 | 2/1990 | Brossi | 548/429 |
| 5,081,117 | 1/1992 | Glamkowski et al. | 548/429 |

FOREIGN PATENT DOCUMENTS

| | | |
|---|---|---|
| 0 154 864 | 9/1985 | European Pat. Off. . |
| 0253372 | 1/1988 | European Pat. Off. . |

OTHER PUBLICATIONS

Yu et al., J. Med. Chem., vol. 31, pp. 2297–2300 (1988).
Atack et al., J. Pharm. Exp. Ther., vol. 249, No. 3., pp. 194–202 (1989).
Yu et al., Heterocycles, vol. 27, No. 3, pp. 745–750 (1988).
Marta et al., Chemical Abstracts vol. 110, No. 9, Abst. 69253 (1989).
Yu et al., FEBS Lett., vol. 234, No. 1, pp. 127–130 (1988).
Yu, Qian–sheng et al. *Helvetica Chimca ACTA*, vol. 74, (1991) pp. 761–766.
Beilstein, Ed. II, vol. 23, 1954, p. 333.

*Primary Examiner*—Johann Richter
*Assistant Examiner*—Taofiq A. Solola
*Attorney, Agent, or Firm*—Gibbons, Del Deo, Dolan, Griffinger & Vecchione

[57] ABSTRACT

The present invention relates to eseroline, $N^1$-noreseroline, and $N^1$-benzylnoreseroline phenyl carbamate analogues which provide highly potent and selective cholinergic agonist and blocking activity and their use as pharmaceutical agents. The invention further relates to improvements in therapeutic methods related to diseases such as glaucoma, myasthenia gravis, alzheimer's disease and to improvements in therapy related to organophosphate poisoning. The invention further provides for selective acetyl-cholinesterase and butyrylcholinesterase agents and a method for inhibiting these esterases.

17 Claims, 1 Drawing Sheet

PHENYLCARBAMATES OF (−)-ESEROLINE, (−)-N1-NORESEROLINE AND (−)-N1-BENZYLNORESEROLINE: SELECTIVE INHIBITORS OF ACETYL AND BUTYRYLCHOLINESTERASE, PHARMACEUTICAL COMPOSITIONS AND METHOD OF USE THEREOF

This application is a continuation of application Ser. No. 07/861,329 filed Mar. 31, 1992, abandoned which is a continuation-in-part of Ser. No. 07/765,746 filed Sep. 26, 1991 now U.S. Pat. No. 5,171,750.

TECHNICAL FIELD

The present invention relates to improvements in the treatment of diseases, and more particularly to compounds which exhibit selective inhibition of acetylcholinesterase and butyrylcholinesterase.

BACKGROUND ART

Physostigmine, also called eserine, and particular derivatives of physostigmine are anti-cholinesterase inhibitors which are well known. Such well known compounds are also useful in the treatment of glaucoma, Myasthenia Gravis, Alzheimer's disease and as antidotes against poisoning with organophosphates.

It has been discovered that the natural isomer of physostigmine has blocking properties as well as agonist properties at the neuromuscular AChR. By contrast (+)-physostigmine shows only negligible inhibition of cholinesterase (ChE). See Brossi et al., FEBS Lett., Vol. 201, pages 190–192 (1986).

Even though (+)-physostigmine has only negligible ChE inhibitory activity, it is as effective as a protective pretreatment drug against multiple lethal doses of sarin, see Albuquerque et al, Fundam. Appl. Caltoxicol., Vol. 5, pages 182–203 (1985). The observed beneficial protection appears to be due to direct interactions of the carbamates with the postsynaptic nicotinic AChR. The protective effectiveness of the carbamates against organo-phosphates appears to be related to the direct ability of the carbamates to decrease the hyperactivation caused by accumulation of the neurotransmitter.

The above information, available due to the research in this field, is important in the evaluation of potential new pharmacological agents for treating cholinergic disorders, for example, Myasthenia Gravis and Alzheimer's disease. Potential agents can be evaluated for potency in vitro by testing the agents against electric eel acetylcholinesterase (AChE) and human plasma butyrylcholinesterase (BChE).

Of the two enzymes known to hydrolyze acetyl-choline (ACh) in vivo, AChE, which is found in red blood cells, in the brain and in nerve tissues, seems to be more specific than BChE which is found in serum, pancreas and in the liver. It, however, has not previously been shown in the art that compounds which selectively inhibit one of the two enzymes more than the other would offer a medical advantage. The natural alkaloid (−)-physostigmine, its potential metabolite (−)-(N1)-norphysostigmine, and the natural alkaloid physovenine which are used as biological standards in this art area, inhibit AChE and BChE in vitro similarly at similar concentrations.

Accordingly, there is need in the art for highly selective agents active against one of AChE and BChE while not being potent against the other so as to lead to better treatment of a particular cholinergic disorder and minimize negative side effects. Such compounds would be of great medical importance in the treatment of cholinergic disorders.

SUMMARY OF THE INVENTION

It is another object of the present invention to provide highly potent and selective cholinergic agonist and blocking compounds.

It is a further object of the present invention to provide improvements in therapy relative to cholinergic diseases such as glaucoma, Myasthenia Gravis, Alzheimer's disease, and organophosphate poisoning.

It is a still further object of the present invention to provide compounds with selective acetylcholinesterase and butyrylcholinesterase activity.

It is a yet further object of the present invention to provide compounds having the following formula:

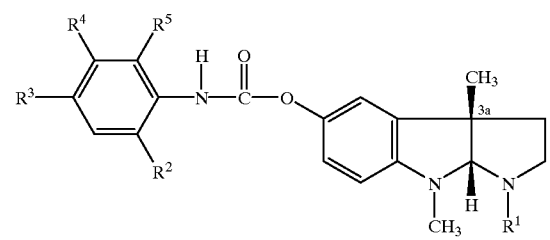

wherein $R^1$ is H, a —$CH_3$ group or a benzyl group;
$R^2$ is straight or branched chained $C_1$–$C_{10}$ alkyl;
$R^3$ is H or straight or branched chained $C_1$–$C_{10}$ alkyl; and
$R^4$ and $R^5$ are independently hydrogen or $R^4$ and $R^5$ taken together along with the carbon atoms to which they are attached form a 6-membered aromatic hydrocarbon ring;
including isomeric forms and pharmaceutically acceptable salts.

DESCRIPTION OF THE PREFERRED EMBODIMENTS

Figure 1:
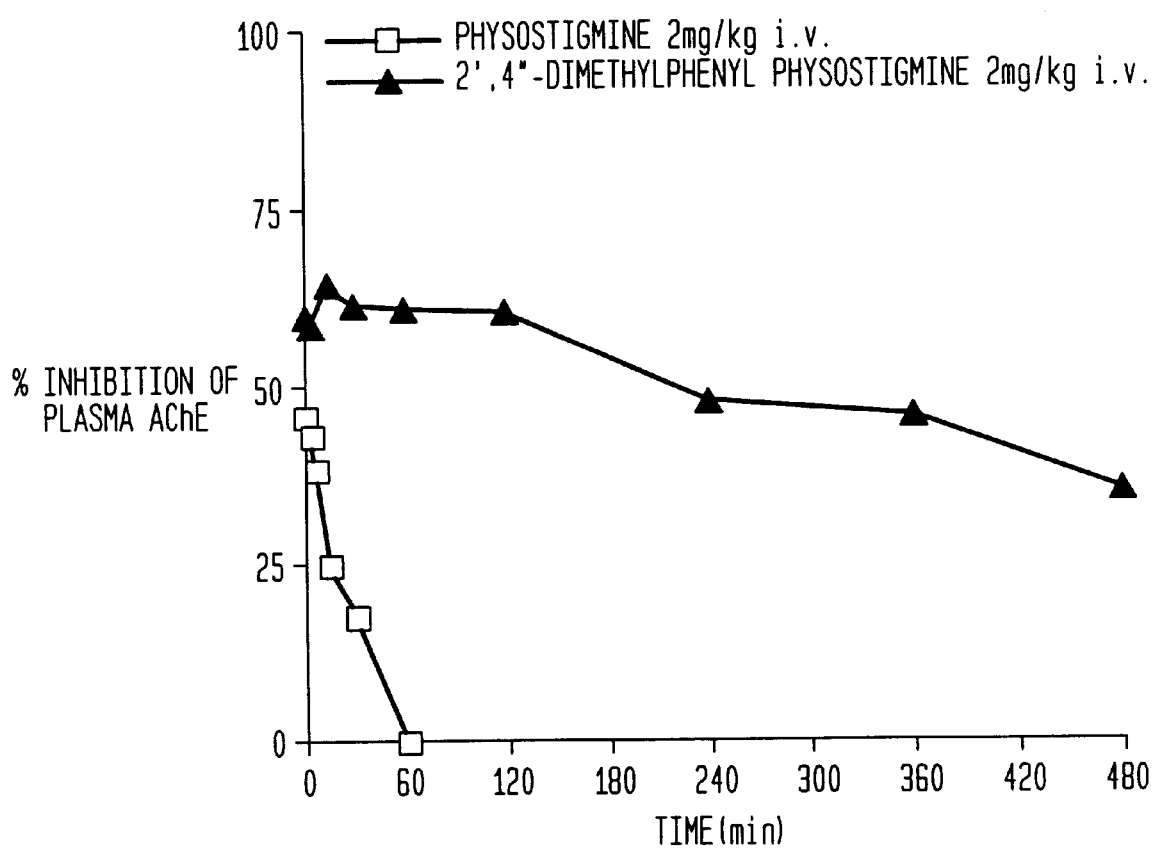
FIG. 1 illustrates the time-dependent inhibition of plasma AChE in a rat host by physostigmine and its 2',4'-dimethylphenyl carbamate.

In accordance with this invention there are disclosed compounds of the formula

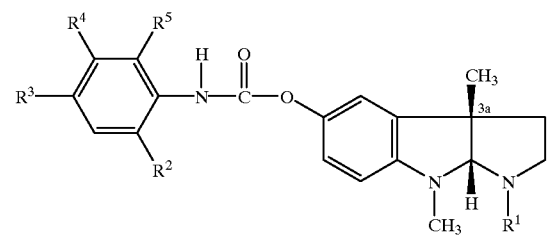

wherein $R^1$ is H, a —$CH_3$ group or a benzyl group;
$R^2$ is straight or branched chained $C_1$–$C_{10}$ alkyl;
$R^3$ is H or straight or branched chained $C_1$–$C_{10}$ alkyl; and
$R^4$ and $R^5$ are independently hydrogen or $R^4$ and $R^5$ taken together along with the carbon atoms to which they are attached form a 6-membered aromatic carbocyclic ring;

including isomeric forms and pharmaceutically acceptable salts. Acceptable salts are salts such as tartrates, fumarates, phosphates, salicylates, and the like.

Preferred are compounds of Formula I, wherein $R^4$ and $R^5$ are both hydrogen.

Even more preferred are compounds wherein $R^3$ is hydrogen and $R^2$ is $C_1$–$C_{10}$ alkyl.

Even more preferred are two groups, R—$CH_3$, —$CH_2$—$CH_3$, —$CH_2$—$CH_2$—$CH_3$— and —$CH(—CH_3)_2$.

The above compounds are eseroline and (1) N-noreseroline carbamates having high potency in the inhibition of acetylcholinesterase and butyryl-cholinesterase. Some of the carbamates were more specific for AChE, whereas others were more highly specific for BChE.

Other cholinesterase inhibitors are known in the prior art. Physostigmine and physovenine are optically active alkaloids with a (3aS)-absolute configuration at the chiral carbon atom C(3a). Both of these compounds are potent inhibitors of cholinesterases in vitro and in vivo, blocking the conversion of acetylcholine into choline reversibly. Physostigmine has been found to have useful medical applications in disorders which result in a malfunction of this process.

Surprisingly, the carbamates according to the present invention have shown high potency. Thus, phenylcarbamate derivatives according to the present invention are longer lasting and appear to be less toxic than other carbamate analoges in this art. Accordingly, the present compounds represent a significant advancement in the prior art.

Compositions within the scope of the invention include compositions wherein the active ingredient is contained in an effective amount to achieve its intended purpose. The compounds can be administered in any pharmaceutically acceptable amount, for example, in amounts ranging from 0.001 gram to about 1 gram per kilogram of body weight. Based on the information which is presented herein, the determination of effective amounts is well within the skill of the ordinary practitioner in the art. The compounds are generally used in pharmaceutical compositions (wt %) containing the active ingredient with a carrier or vehicle in the composition in an amount of about 0.1 to 99 wt % and preferably about 25–85 wt %.

Either fluid or solid unit dosage forms can be readily prepared for oral administration. For example, the compounds of Formula I can be admixed with conventional ingredients such as dicalcium phosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. In older or incoherent patients sustained release formulations may even be preferred. Capsules may be formulated by mixing the compound with a pharmaceutical diluent which is inert and inserting this mixture into a hard gelatin capsule having the appropriate size. If soft capsules are desired, a slurry of the compound with an acceptable vegetable, light petroleum or other inert oil can be encapsulated by forming into a gelatin capsule.

Suspensions, syrups and elixirs may be used for oral administration of fluid unit dosage forms. A fluid preparation including oil may be used for oil soluble forms. A vegetable oil such as corn oil, peanut oil or safflower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener (such as sugar, saccharin, or a biological sweetener) and a flavoring agent in the form of an elixir.

Pharmaceutical compositions for parenteral and suppository administration can also be obtained using techniques standard in the art.

Preferred uses of the compounds according to the invention are as pharmaceutical agents suitable for oral administration. Another preferred use of the compounds is in transdermal parenteral formulations, which are particularly useful in treating cholinergic disorders such as glaucoma, Myasthenia Gravis, Alzheimer's disease, and organophosphate poisoning. Accordingly, compositions suitable for administration to these areas are particularly included within the invention. The above parenteral solutions or suspensions may be administered transdermally and delivered with a skin patch. If desired they may be given by injection in an appropriate vehicle such as sesame oil.

Accordingly, incorporation of the active compounds and a slow release matrix may be implemented for administering transdermally. The compounds may be administered transdermally in amounts of about 0.01 to 99% of the composition and preferably about 25 to 85 wt % of the active ingredient in the vehicle or carrier.

Transdermal therapeutic systems are self-contained dosage forms that, when applied to intact skin, deliver drug(s) at a controlled rate to the systemic circulation. Advantages of using the transdermal routing include: enhanced therapeutic efficacy, reduction in the frequency of dosing, reduction of side effects due to optimization of blood-concentration vs. time profile, increased patient compliance due to elimination of multiple dosing schedules, bypassing the hepatic "first pass" metabolism, avoiding gastrointestinal incompatibilities and providing a predictable and extendable duration of activity. However, the main function of the skin is to act as a barrier to entering compounds. As a consequence, transdermal therapy has been preferred for a limited number of drugs that possess the desirable physiochemical properties for diffusion across the skin barrier. One effective method of overcoming the barrier function of the skin is to include a penetration enhancer in the formulation of the transdermal therapeutic system.

The penetration enhancer is a chemical compound that, when included in a formulation, temporarily increases the permeability of the skin to a drug line allowing more of the drug to be absorbed in a shorter period of time. Several different types of penetration enhancers have been reported such as dimethylsulfoxide, n-decylmethylsulfoxide, N,N-dimethylacetamide, N,N-dimethylformamide, 1-dodecylazacycloheptane-2-one (Azone), propylene glycol, ethanol, pyrrolidones such as N-methyl-2-pyrrolidone (NMP) and surfactants.

The above compounds can be present in the reservoir alone or in combination with pharmaceutical carriers. The pharmaceutical carriers acceptable for the purposes of this invention are the known art carriers that do not adversely effect the drug, the host, or the material comprising the drug delivery device. Suitable pharmaceutical carriers include sterile water, saline, dextrose, dextrose in water or saline; condensation products of castor oil and ethylene oxide combining about 30 to 35 moles of ethylene oxide per mole of castor oil, liquid acid, lower alkanols, oils such as corn oil, peanut oil, sesame oil and the like, with emulsifiers such as mono- or di- glyceride of a fatty acid; or a phosphatide, e.g., lecithin, and the like; glycols, polyalkylene glycols, aqueous media in the presence of a suspending agent, for example, sodium carboxymethyl cellulose, sodium alginate, poly(vinylpyrrolidone), and the like, alone, or with suitable dispensing agents such as lecithin, polyoxyethylene stearate, and the like. The carrier may also contain adjuvants such as preserving agents, stabilizing agents, wetting agents, emulsifying agents and the like together with penetration enhancer and the compounds of this invention.

The effective dose for mammals may vary due to such factors as age, weight, activity level or condition of the subject being treated. Typically, an effective dosage of a compound according to the present invention is about 1 to 800 milligrams when administered by either oral or rectal dose from 1 to 3 times daily. This is about 0.002 to about 50 milligrams per kilogram of the subject's weight administered per day. Preferably about 10 to about 300 milligrams are administered orally or rectally 1 to 3 times a day for an adult human. The required dose is considerably less when administered parenterally. Preferably about 0.01 to about 150 milligrams may be administered intra-muscularly or transdermally, one or two times a day for an adult human.

Compounds of the present invention may be administered topically in amounts of about 0.01 to about 99 wt % of the composition, and preferably about 25 to 85 wt %. The present compounds are also useful in a method for treating cholinergic disorders such as glaucoma, Myasthenia Gravis, Alzheimer's disease, and as an antidote against poisoning with organo phosphates. The method according to the invention comprises administering an effective amount of a compound according to the invention or an effective amount of a pharmaceutical composition according to the invention to a mammal in need of such treatment.

Surprisingly, the compounds according to the invention have shown selective cholinergic agonist and blocking activity. Of the two enzymes known to hydrolyze acetylcholine in vivo, acetylcholinesterase (AChE) which is found in red blood cells, in the brain, and in nerve tissues, seems to be more specific then butyrylcholinesterase (BChE) which is found in serum, pancreas and in the liver. It, however, was never shown that compounds which selectively inhibit one of the two enzymes more than the other, would offer a medical advantage. The selectivity of the enzyme inhibition, as shown with the inactive carbamates (-)-4'-methylphenylcarbamoyleseroline, (-)-2',6'-diethylphenylcarbamoyleseroline, and (-)-2',4',6'-trimethylphenylcarbamoyleseroline, depends on the substitution in the phenyl ring of the phenylcarbamate group.

The present invention relates to selective inhibition as follows: The natural alkaloid (-)-physostigmine, its potential metabolite (-)-(N1)-norphysostigmine and the natural alkaloid physovenine which were used as biological standards in the inhibited AChE and BChE in vitro similarly at similar concentrations.

Reaction of phenols having the natural (3aS)-absolute configuration, i.e., (-)-eseroline, (-)-(N1)-noreseroline, or (-)-(N1)-benzylnoreseroline with commercially available isocyanates in dry ether and in the presence of a catalytic amount of sodium, afforded the desired carbamates. See Reaction Scheme 1, below. They were separated from "dimers", which invariably formed, by chromatography, and removed as the faster running materials. The structures of the carbamates which often were amorphous were secured by MS and $^1$H-NMR spectra, and they were characterized by TLC-analysis and by optical rotation. Details of the preparation of the carbamates according to the present invention are given in the experimental section. Conversion of the (N1)-protected carbamates into compounds of the (N1)-series was accomplished by catalytic hydrogenation over Pd(OH)$_2$ catalyst as shown in Scheme 2 and described below.

The resulting phenylcarbamates, which all have the natural (3aS)-absolute configuration, are listed below in Table 1, following the illustration of reaction Schemes 1 and 2.

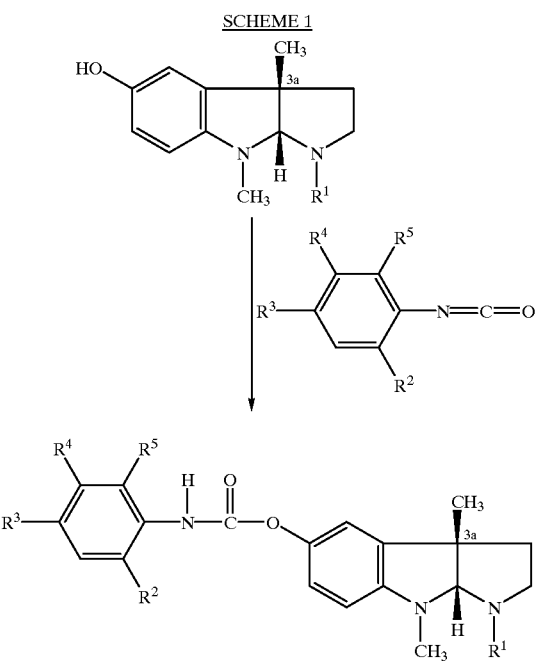

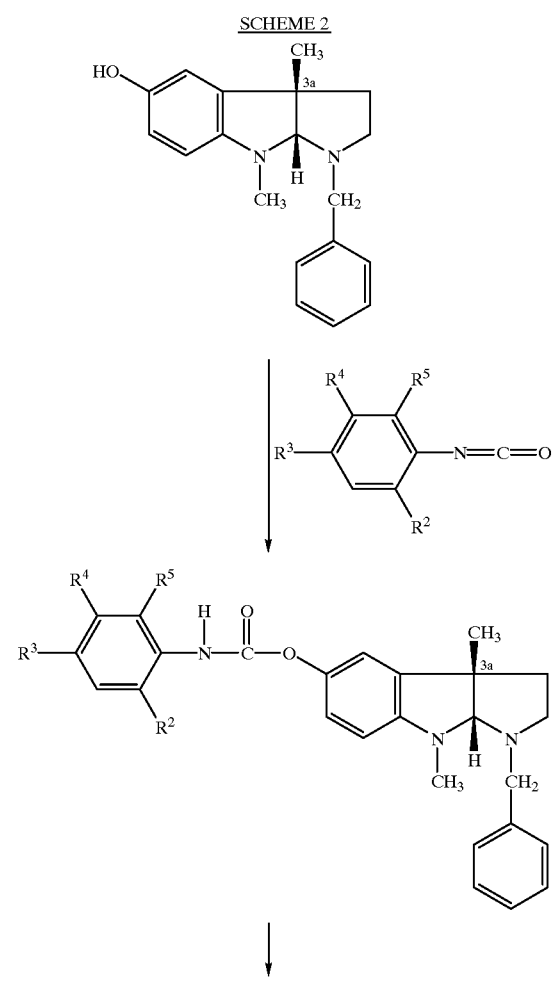

-continued

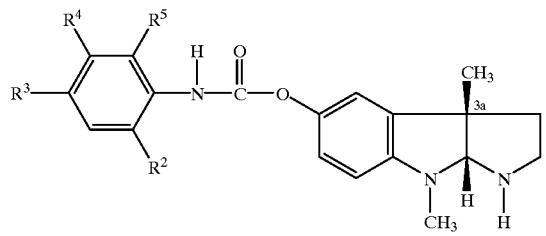

The following compounds are provided

TABLE 1

| | $R^4,R^5$ | $R^1$ | $R^2$ | $R^3$ |
|---|---|---|---|---|
| 1. | —H,—H | —CH$_3$ | —CH$_3$ | —H |
| 2. | —H,—H | —CH$_3$ | —CH$_3$ | —CH$_3$ |
| 3. | —H,—H | —CH$_3$ | —H | —CH(—CH$_3$)$_2$ |
| 4. | —H,—H | CH$_3$ | —CH$_2$—CH$_3$ | —H |
| 5. | —H,—H | —CH$_3$ | —CH(CH$_3$)$_2$ | —H |
| 6. | ⌬ | —CH$_3$ | —H | —H |
| 7. | —H,—H | —CH$_2$—Ph | —CH$_3$ | —H |
| 8. | —H,—H | —CH$_2$—Ph | —CH$_3$ | —CH$_3$ |
| 9. | —H,—H | —CH$_2$—Ph | —H | —CH(CH$_3$)$_2$ |
| 10. | —H,—H | —CH$_2$—Ph | —H | —H |
| 11. | —H,—H | —H | —CH$_3$ | —H |
| 12. | —H,—H | —H | —CH$_3$ | —CH$_3$ |
| 13. | —H,—H | —H | —H | —CH(CH$_3$)$_2$ |
| 14. | —H,—H | —H | —H | —H |
| A'. | —H,—H | —CH$_3$ | —H | —CH$_3$ |
| B'. | —H,—CH$_2$CH$_3$ | —CH$_3$ | —CH$_2$—CH$_3$ | —H |
| C'. | —H,—CH$_3$ | —CH$_3$ | —CH$_3$ | —CH$_3$ |

Experimental

Melting points (uncorrected): Fisher-Johns apparatus; optical rotations ($[a]_D$, CHCl$_3$: Perkin-Elmer-241 MC automatic polarimeter, IR spectra (cm$^{-1}$, CHCl$_3$): Beckman-IR-4230 instrument, BIO-RAD FTS-45 instrument; $^1$H NMR (in CDCl$_1$ with Me$_4$Si as internal reference, δ ppm, J Hz): Varian XL-300 MHz, Gemini 300 MHz spectrometer, MS (m/z) for chemical ionization (CI): Finnigan-1015D mass spectrometer, for electron impact (EI): V.G. Micromass 7070 mass spectrometer, for HR MS (FAB): JEOL JMS-SX 102 magnetic sector mass spectrometer thin layer chromatography (silica gel GHLF), 250 μm): Analtech Inc.; column chromatography (silica gel GHLF, 250 μm); Merck 60 (230–400 mesh); the solvent systems used for TLC analysis were the following: CH$_2$Cl$_2$/5% MeOH; CH$_2$Cl$_2$/10% MeOH; the solvent systems used for column chromatography: CH$_2$Cl$_2$/5% MeOH(A); CH$_2$Cl$_2$/10% MeOH(B).

EXAMPLE 1

(−)-2'-Methylphenylcarbamoyleseroline (−)-Eseroline 0 (0.12 g, 0.55 mmol) was dissolved in anhydrous Et$_2$O (10 mL) and a small piece of Na metal was added. After stirring for about 2 min at room temperature under nitrogen, 2'-methylphenylisocyanate (0.09 g, 0.70 mmol) was added dropwise. After complete addition the solvent was evaporated immediately. The residue was flash chromatographed on a silica gel column (system B) to give (−)-2'-methylphenylcarbamoyleseroline as a foam (0.88 g, 46%); $[a]_D$−69.6° (c=0.5, CHCl$_3$), CI MS (m/z): 352 (M$^+$+1); EI MS (m/z): 351 (M$^+$), HR MS (FAB) calcd for (M$^+$+1) C$_{21}$H$_{26}$N$_3$O$_2$ 352.2025, found 352.2020, IR; 3410, 2930, 1745; $^1$H NMR 1.46 (s, 3H, C10-CH$_3$), 1.90–2.12 (m 2H, c3-H), 2.32 (s, 3H, Me—Ph), 2.55 (s, 3H, N1-CH$_3$, 2.58–2.70 (m, 2H, C2-H$_2$), 2.91 (s, 3H, N*—CH$_3$), 4.18 (s, 1H, C9-H), 6.33 (d, J=8.4, 1H, C7-H), 6.63 (br s, 1H, N—H), 6.85–6.95 (m, 2H, C4-H, C6-H), 7.05 (t, J=1H, C5'-H), 7.15–7.23 (m, CH, CH3'-H, C6'-H), 7.85 (br s, 1H, C4'-H).

All other carbamates: (−)-2'-4'-dimethylphenylcarbamoyleseroline, 4'-isopropylcarbamoyleseroline, (−)-2'-ethylphenylcarbamoyleseroline, (−)-2'isopropylphenylcarbamoyleseroline, naphthylcarbamoyleseroline, were similarly prepared from (−)-eseroline with the corresponding isocyanates. The important physical data for these compounds are shown below.

EXAMPLE 2

(−)-2'-4'-Dimethylphenyl-carbamoyleseroline

The important data is as follows: a foam, $[a]_D$−79.6° (c=1, CHCl$_3$), CI MS (m/z): 366; $^1$H NMR 2.28 (s, 3H, C2'-CH$_3$), 2.29 (s, 3H, C4'-CH$_3$).

EXAMPLE 3

(−)-4'-Isopropylphenylcarbamoyleseroline

The important data is as follows: m.p. (° C.) 152–153 $[a]_D$ −67.8° (c=1, CHCl$_3$) CI MS (m/z) 380 (M$^+$=1); HR MS (FAB): calcd for (M$^+$+1) C$_{23}$H$_{30}$N$_3$O$_2$, 380.2338; $^1$H-NMR: 1.23 (d, J=6.8, 6H, CH(CH$_3$)$_2$.

EXAMPLE 4

(−)-2'-Ethylphenylcarbamoyleseroline

The important data is as follows: a foam, $[a]_D$ −62.8° (c=1, CHCl$_3$) CI MS (m/z) 366 (M$^+$=1); HR MS (FAB): calcd for (M$^+$+1) C$_{22}$H$_{28}$N$_3$O$_2$, 366.2182; $^1$H-NMR: 1.26(t, J=7.5, 3H, —CH$_2$—CH$_3$), 2.55–2.78 (m, 4H, C2-H, —CH$_2$—CH$_3$).

EXAMPLE 5

(−)-2'-Isopropylphenylcarbamoyleseroline

The important data is as follows: a foam, $[a]_D$ −58.8° (c=1, CHCl$_3$) CI MS (m/z) 380 (M$^+$=1); HR MS (FAB): calcd for (M$^+$+1) C$_{23}$H$_{29}$N$_3$O$_2$, 379.2259; $^1$H-NMR: 1.30(d, J=6.8, 6H, —CH—(CH$_3$)$_2$).

EXAMPLE 6

(−)-1-Naphthylcarbamoyleseroline

The important data is as follows: a foam, $[a]_D$ −62.0° (c=1, CHCl$_3$) CI MS (m/z) 388 (M$^+$=1); HR MS (FAB): calcd for (M$^+$+1) C$_{24}$H$_{26}$N$_3$O$_2$, 388.2025; $^1$H-NMR: 7.51 (m,3H), 7.69 (d, J=8.1, 1H), 7.89 (d, J=7.5, 1H), 7.96 (d, J=7.9, 2H).

The related carbamates: (−)-2'methylphenylcarbamoyl-N1-noreseroline, (−)-2',4'-dimethylphenylcarbamoyl-N1-noreseroline, and (−)-4'-isopropylphenylcarbamoyl-N1-noreseroline and (−)-phenylcarbamoyl-N1-noreseroline were similarly prepared from (−)-(N1)-benzylnoreseroline instead of eseroline by reacting (−)-(N1)-benzylnoreseroline with the corresponding isocyanates. The benzyl protecting group was then removed to yield the noreseroline compound from the benzylnoreseroline compound.

The following example shows the removal of a benzyl protecting group from (−)-2'-methylphenylcarbamoyl-(N1)-benzylinoreseroline to yield compound (−)-2'-methylphenylcarbamoyl-(N1)-noreseroline.

EXAMPLE 7

(−)-2'-Methylphenylcarbamoyl-N1-benzylnoreseroline ($N^1$)-Benzylnoreseroline (2.0 g) was dissolved in anhydrous $Et_2O$ (10 ml), and a small piece of Na added. After stirring for 2 minutes at room temperature under nitrogen, 2-methylphenyl isocyanate was added (0.04 g). After stirring for 15 minutes the solvent was evaporated and the residue was chromatographed to give the carbamate as a foam: $[a]_D$ −62.0° (c=0.5, $CHCl_3$); CI MS (m/z) 428 ($M^+$+1).

EXAMPLES 8–10

The carbamates of Examples 8–10 belonging to the (−)-$N^1$-benzylnoreseroline series have been prepared from (−)-$N^1$-benzylnoreseroline and isocyanates as described in Example 7. The important physical data is as follows.

EXAMPLE 8

(−)-2'-4'-Dimethylphenylcarbamoyl-(N1)-benzylnoreseroline

The important data is as follows: a foam, $[a]_D$ −58.4° (c=0.5 $CHCl_3$), CI MS (m/z): 442; $^1$H NMR 2.28 (2s, 6H), 3.91 (dd, 2H).

EXAMPLE 9

(−)-4'-Isopropylphenylcarbamoyl-(N1)-benzylnoreseroline

The important data is as follows: a foam, $[a]_D$ −44.8° (c=0.5, $CHCl_3$) CI MS (m/z) 456 ($M^+$+1); $^1$H-NMR: 1.24 (d, J=7.0, 6H), 3.94 (dd, 2H).

EXAMPLE 10

(−)-Phenylcarbamoyl-(N1)-benzylnoreseroline

The important data is as follows: m.p. (° C.) 158–159, $[a]_D$ −56.4° (c=0.5, $CHCl_3$) CI MS (m/z) 414 ($M^+$+1); $^1$H-NMR: 3.92 (dd, 2H).

EXAMPLE 11

(−)-2'-Methylphenylcarbamoyl-N1-noreseroline (−)-2'-Methylphenylcarbamoyl-N1-benzylnoreseroline (0.09 g, 0.21 mmol) from Example 7 was dissolved in MeOH (10 mL), and palladium hydroxide on carbon (7 mg) was added. After hydrogenation under atmospheric pressure for 5 h, the palladium catalyst was filtered through Celite and the solvent was evaporated in vacuo. The residue was chromatographed by preparative TLC (silica gel plate 2000 µm, $CH_2Cl_2$/10% MeOH) to give (−)-2'-methylphenylcarbamoyl-N1-noreseroline as a foam (0.04 g, 56%): $[\alpha]_D$ −62.4° (c=0.5, $CHCl_3$), CI MS (m/z):338 ($M^+$+1); EI MS (m/z): 337 ($M^+$), HR MS (EI) ($M^+$) calcd, for $C_{20}H_{23}N_3O_2$ 337.1790, found 337.1776 $^1$H NMR: 1.42 (s,3H, C10-$CH_3$), 1.70–1.80 (m, 1H, C3-H), 1.95–2.08 (m, 1H, C2-H), 2.29 (s, 3H, C2'-$CH_3$), 2.70–2.80 (m, 1H, C2-H), 2.81 (s, 1H, N8-$CH_3$), 3.01–3.10 (ddd, J=2.5, 2.5, 2.5, 1H, C2-H), 4.51 (s, 1H, C9-H), 6.25 (d, J=9.0, 1H, C7-H), 6.63 (br s, 1H, N—H), 6.83–6.86 (m, 2H, C4-H, C6-H), 7.02 (t, J -7.5, 1H, C5'-H), 7.15–7.22 (m, 2H, C3'-H, C6'-H), 7.85 (br s, 1H, C4'-H).

EXAMPLES 12–14

The carbamates of Examples 12–14, belonging to the (−)-$N^1$-noreseroline series, were prepared from Examples 8–10, belonging to the (−)-$N^1$-benzylnoreseroline series, by catalytic debenzylation as described in Example 10. The important physical data is as follows.

EXAMPLE 12

(−)-2'-4'-Dimethylphenylcarbamoyl-(N1)-noreseroline

The important data is as follows: a foam, $[a]_D$ −55.4° (c=0.5 $CHCl_3$), CI MS (m/z): 352; $^1$H NMR 2.45 (2s, 6H).

EXAMPLE 13

(−)-4'-Isopropylphenylcarbamoyl-(N1)-noreseroline

The important data is as follows: m.p. (° C.) 82–84, $[a]_D$ −43.5° (c=0.5, $CHCl_3$) CI MS (m/z) 366 ($M^+$+1); $^1$NMR: 1.23 (d, J=7.0, 6H).

EXAMPLE 14

(−)-Phenylcarbamoyl-(N1)-noreseroline

The important data is as follows: m.p. (° C.) 129–131, $[a]_D$ −50.4° (c=0.5, $CHCl_3$) CI MS (m/z) 324 ($M^+$+1); $^1$NMR: 7.25–7.52 (m, 5H).

The following inactive compounds were provided using the above method.

EXAMPLE A'

(−)-4'-methylphenylcarbamoyleseroline

The important data is as follows: m.p. (° C.) 143–145 $[a]_D$ −74.2° (c=1, $CHCl_3$) CI MS (m/z) 352 ($M^+$=1); HR MS (FAB): calcd for ($M^+$+1) $C_{21}H_{26}N_3O_2$, 352.2025 $^1$H-NMR: 2.31 (s,3H, C4'-$CH_3$).

EXAMPLE B'

(−)-2',6'-diethylphenylcarbamoyleseroline

The important data is as follows: an oil, $[a]_D$ −36.1° (c=1, $CHCl_3$) CI MS (m/z) 394 ($M^+$=1); HR MS (FAB): calcd for ($M^+$+1) $C_{21}H_{26}N_3O_2$, 394.2495; $^1$H-NMR: 1.24 (t, J=7.4, 6H, 2-$CH_2$—$CH_3$), 2.68 (m, 6H, C2-H, 2-$CH_2CH_3$)

EXAMPLE C'

(−)-2',4',6'-trimethylphenylcarbamoyleseroline

The important data is as follows: a foam, $[a]_D$ −55.8° (c=1, $CHCl_3$) CI MS (m/z) 380 ($M^+$=1); $^1$H-NMR: 2.28(3s, 9H, C2', C4', C6'—$CH_3$).

The comparative (−)-phenylcarbamoyleseroline compound ((−)-phenserine) was provided as follows.

EXAMPLE D'

(−)-Phenylcarbamoyleseroline (−)-Eseroline 0 (0.12 g, 0.55 mmol) was dissolved in anhydrous $Et_2O$ (10 mL) and a small piece of Na metal was added. After stirring for about 2 min at room temperature under nitrogen, phenylisocyanate (0.09 g, 0.70 mmol) was added dropwise. After complete addition the solvent was evaporated immediately. The residue was flash chromatographed on a silica gel column (system B) to give (−)-phenylcarbamoyleseroline mp(° C.) 142–143 (0.88 g, 46%); $[a]_D$ −74.2° (c=1, $CHCl_3$), CI MS (m/z): 338; $^1H$ NMR 7.01 (t, J=7.4, 1H, C4'-H), 7.22 (t, J7.4, 2H, C3'-H, C5'-H), 7.34 (d, J=7.4, 2H, C2'-H, C6'-H). The common name for this compound is (−)-phenserine.

The compound numbers in Tables I and II correspond to one another and to the above Examples. Comparative Example D' is (−)-Phenserine.

In vitro Assay of Human Anti-AChE and -BChE Activity, $IC_{50}$

A classical enzyme inhibition assay was undertaken to quantitate the activity of the derivatives against AChE and BChE. Anti-cholinesterase activity was determined against human erythrocyte AChE and plasma BChE in 0.1 M $Na_3PO_4$ buffer (pH 8.0) using the spectrophotometric method of Ellman et al. (Biochem. Pharmacol. 7:88, 1961). Freshly collected plasma was diluted 1.125 with 0.1 M $Na_3PO_4$ (pH 7.4) and lysed erythrocytes similarly diluted to 1:200. Acetyl-B-methylthiocholine (0.5 mM) and s-butyrylthiocholine (0.5 mM) were used as specific substrates for AChE and BChE, respectively, 25 μl of substrate and 25 μl of enzyme in a total volume of 0.75 ml.

Physostigmine derivatives, diluted in half log-intervals to a concentration range of between $1\times10^{-5}M$ and $3\times10^{-10}M$, were preincubated with enzyme (30 min at 21° C.) prior to addition of substrates. Following incubation (30 min at 37° C.), production of a yellow thionitrobenzoate anion was measured with a spectrophotometer set to 412 nm wavelength. Nonspecific substrate hydrolysis was determined under conditions of complete enzyme inhibition (by addition of physostigmine $1\times10^{-5}M$), and the associated change in absorbance subtracted from that observed with the test compounds. Finally, the activity of each compound was assessed alongside that of physostigmine, as an external standard, whose activity has been previously reported (Atack et al., J. Pharm. Expl. Ther. 249:294, 1989).

The AChE and BChE activity of each compound was expressed as an $IC_{50}$, which is defined as the concentration in nmol required to inhibit 50% of enzyme activity (calculated as described by Atack et al., J. Pharm. Expl. Ther. 249:294, 1989)).

In vivo Duration of Activity Studies

Catheters, filled with heparinized saline, were tied into the right femoral vein and artery of anesthetized male rats, which then were restrained in a plaster cast and allowed to recover from anesthesia in a temperature-controlled enclosure. Plasma samples were withdrawn to quantitate untreated levels of AChE activity. At 90 min. after surgery, hexamethonium bromide (5 mg/kg, i.p.) was administered, followed by atropine methylbromide (4 mg/kg, s.c.) 10 min. later. These quaternary nicotinic and muscarinic antagonists, do not enter brain and inhibit peripheral cholinergic overdrive associated with cholinesterase inhibition, which may be deleterious to the animal. Two hours after surgery, either physostigmine or physostigmine derivatives were administered i.v. Plasma samples were removed at intervals between 2 min. and 8 hr., immediately frozen to −70° C. and then assayed for cholinesterase inhibition. AChE inhibition was measured as described above, with necessary modifications required for quantitation from rat plasma.

All drugs were formulated in a manner consistent with i.v. administration. Specifically, drugs were dissolved in Tween 80/EtOH (3:1, V:V), approximately 100 μl, and then were diluted in excess of 1:9 (V:V) with isotonic saline. The use of Tween 80/EtOH did not affect either AChE or BChE inhibitory activity of compounds in in vitro studies (Yu et al., Helv. Chim. Acta 74, pages 761–766, (1991)). Doses were determined in prior studies involving the measurement of rectal temperature and tremor; two centrally-mediated actions of cholinesterase inhibitiors and cholinergic agonists.

FIG. 1 demonstrates the in vivo inhibition of the enzyme acetylcholinesterase (AChE) by physostigmine and its 2',4'-dimethylphenyl carbamate derivative, i.e., the time-dependent activity of these cholinesterase inhibitors in rats. As predicted from the in vitro $IC_{50}$ studies, physostigmine and the substituted phenyl carbamates to which this patent relates (which are represented in this case by 2',4'-dimethylphenyl physostigmine) possess excellent in vivo cholinesterase inhibitory properties. However, the duration of enzyme inhibition is short following an intravenous bolus of physostigmine. Whereas as peak inhibition of 46% occurred within 2 minutes of administration, this rapidly declined to 25% by 15 minutes and was negligible at one hour. An equal dose of the 2'4'-methylphenyl carbamate resulted in immediate 60% AChE inhibiiton at 2 minutes. This was maintained at a steady level for 2 hours and then slowly declined to 36% inhibition at 8 hours. The high activity, specificity and persistence of 2',4'-dimethylphenyl physostigmine, which is achieved without side-effects or toxicity, is surprising and supports the contention that these compounds represent a class of potent, new and selective cholinesterase inhibitors.

Below are shown the structures of comparative compounds A, B, and C whose biological activity is used to compare with the compounds according to the present invention. The comparisons of the compounds according to the invention with these standard compounds and inactive compounds (A', B', C') are set forth in Table 2, following the structures below.

COMPARATIVE COMPOUNDS

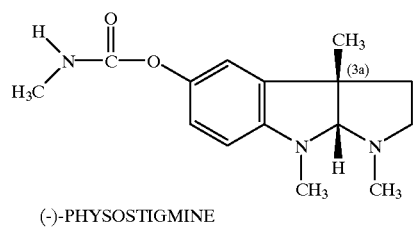

(−)-PHYSOSTIGMINE

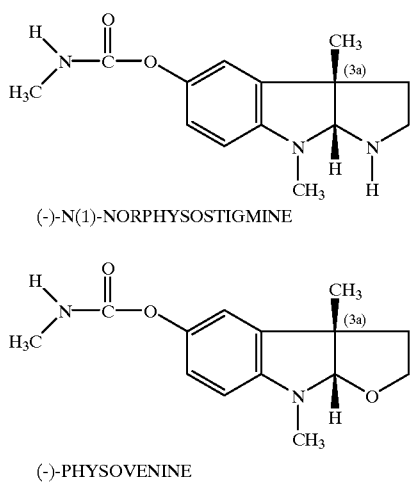

(-)-N(1)-NORPHYSOSTIGMINE (-)-PHYSOVENINE

Table 2

IC$_{50}$ Values of Phenylcarbamates of (-)-Eseroline, (-)-Physovenol, and (-)-N$^1$-Noreseroline vs. Human Erythrocyte AChE and Human Plasma BChE

| No. | Human Erythrocyte AChE | Human Plasma BChE |
|---|---|---|
| Biological Standards | IC$_{50}$ [nmol] | IC$_{50}$ [nmol] |
| A physostigmine | 27.9 ± 2.4 | 16.0 ± 2.9 |
| B N'norphysostigmine | 21.0 ± 1.0s | 2.0 ± 1.0 |
| C physovenine | 27.1 ± 0.8 | 3.7 ± 1.4 |
| D' phenserine | 24.0 ± 6.0 | 1300 ± 85.0 |
| Examples | | |
| Ex. 1 | 10.3 ± 1.6 | 1948.5 ± 245.5 |
| Ex. 2 | 13.6 ± 1.0 | 1817.0 ± 558.5 |
| Ex. 3 | 758.2 ± 21.2 | 51.3 ± 0.9 |
| Ex. 4 | 9.7 ± 0.7 | 2916.0 ± 537.0 |
| Ex. 5 | 15.5 ± 1.3 | 647.8 ± 46.2 |
| Ex. 6 | 16.1 ± 1.0 | 1832.0 ± 35.5 |
| Ex. 7 | not tested | |
| Ex. 8 | not tested | |
| Ex. 9 | >10,000 | 45.3 ± 4.6 |
| Ex. 10 | not tested | |
| Ex. 11 | 17.0 ± 0.2 | 2165.0 ± 85.0 |
| Ex. 12 | 17.3 ± 1.2 | 1139.0 ± 26.0 |
| Ex. 13 | 322.4 ± 3.7 | 8.3 ± 1.0 |
| Ex. 14 | 13.8 ± 0.7 | 612.0 ± 0.4 |
| Inactive Compounds | | |
| Ex. A' | 139.2 ± 3.7 | 251.1 ± 8.6 |
| Ex. B' | 1493.7 ± 49.8 | 1073.5 ± 48.0 |
| Ex. C' | 1291.9 ± 73.8 | 1817.0 ± 885.0 |

The foregoing description of the specific embodiments will so fully reveal the general nature of the invention that others can, by applying current knowledge, readily modify and/or adapt for various applications such specific embodiments without departing from the generic concept and therefore such adaptations are intended to be comprehended within the meaning and range of equivalents of the disclosed embodiments. It is to be understood that the phraseology or terminology employed herein is for the purpose of description only and not of limitation.

We claim:

1. A compound for the selective inhibition of acetylcholinesterase selected from the group consisting of:
(-)-2'-methylphenylcarbamoyleseroline (1),
(-)-2'-methylphenylcarbamoyl-N1-noreseroline (11),
(-)-phenylcarbamoyl-N1-noreseroline (14),
and pharmaceutically acceptable salts thereof.

2. A pharmaceutical composition comprising a pharmaceutically effective amount of at least one compound according to claim 1 and a pharmaceutically acceptable carrier.

3. A method for inhibiting acetylcholinesterase activity comprising administering an effective amount of at least one compound according to claim 1 to a mammal in need thereof.

4. The method according to claim 3, wherein said at least one compound is administered transdermally.

5. A method for treating cholinergic disorders comprising administration of an effective amount of at least one compound according to claim 1 to a mammal in need of such treatment.

6. A method according to claim 5, wherein the cholinergic disorder is selected from the group consisting of glaucoma and Myasthenia Gravis.

7. A method for treating organophosphate poisoning in a mammal comprising administering an effective amount of at least one compound according to claim 1.

8. The compound according to claim 1, wherein said compound is (-)-2'-methylphenylcarbamoyleseroline (1) and pharmaceutically acceptable salts thereof.

9. The compound according to claim 1, wherein said compound is (-)-2'-methylphenylcarbamoyl-N1-noreseroline (11) and pharmaceutically acceptable salts thereof.

10. The compound according to claim 1, wherein said compound is (-)-phenylcarbamoyl-N1-noreseroline (14) and pharmaceutically acceptable salts thereof.

11. A compound for the selective inhibition of acetylcholinesterase selected from the group consisting of
(-)-2',4'-dimethylphenylcarbamoyleseroline (2),
(-)-2'-ethylphenylcarbamoyleseroline (4),
(-)-2'-isopropylphenylcarbamoyleseroline (5),
(-)-2',4'-dimethylphenylcarbamoyl-N1-noreseroline (12),
and pharmaceutically acceptable salts thereof.

12. A pharmaceutical composition comprising a pharmaceutically effective amount of at least one compound according to claim 11 and a pharmaceutically acceptable carrier.

13. A method for inhibiting acetylcholinesterase activity comprising administering an effective amount of at least one compound according to claim 11 to a mammal in need thereof.

14. The method according to claim 13, wherein said at least one compound is administered transdermally.

15. A method for treating cholinergic disorders comprising administration of an effective amount of at least one compound according to claim 11 to a mammal in need of such treatment.

16. A method according to claim 15, wherein the cholinergic disorder is selected from the group consisting of glaucoma and Myasthenia Gravis.

17. A method for treating organophosphate poisoning in a mammal comprising administering an effective amount of at least one compound according to claim 11.

* * * * *